United States Patent
Taylor et al.

(10) Patent No.: US 9,886,752 B2
(45) Date of Patent: Feb. 6, 2018

(54) VISION-BASED GRADING WITH AUTOMATIC WEIGHT CALIBRATION

(71) Applicant: Laitram, L.L.C., Harahan, LA (US)

(72) Inventors: Bruce F. Taylor, Kenner, LA (US); Robert S. Lapeyre, New Orleans, LA (US)

(73) Assignee: Laitram, L.L.C., Harahan, LA (US)

(*) Notice: Subject to any disclaimer, the term of this patent is extended or adjusted under 35 U.S.C. 154(b) by 43 days.

(21) Appl. No.: 15/016,568

(22) Filed: Feb. 5, 2016

(65) Prior Publication Data

US 2016/0232656 A1 Aug. 11, 2016

Related U.S. Application Data

(60) Provisional application No. 62/112,490, filed on Feb. 5, 2015.

(51) Int. Cl.
| | |
|---|---|
| G06K 9/00 | (2006.01) |
| G06T 7/00 | (2017.01) |
| G01G 17/00 | (2006.01) |
| G01N 33/02 | (2006.01) |
| G06K 9/62 | (2006.01) |
| G01G 17/08 | (2006.01) |

(52) U.S. Cl.
CPC ........... *G06T 7/0004* (2013.01); *G01G 17/00* (2013.01); *G01G 17/08* (2013.01); *G01N 33/02* (2013.01); *G06K 9/6202* (2013.01); *G06T 2207/30128* (2013.01); *G06T 2207/30242* (2013.01)

(58) Field of Classification Search
USPC ........... 382/110, 218, 220; 1/1; 83/422, 423, 83/865; 408/111, 207; 434/127; 604/66, 604/504
See application file for complete search history.

(56) References Cited

U.S. PATENT DOCUMENTS

| | | |
|---|---|---|
| 2,964,181 A | 12/1960 | Demarest et al. |
| 4,586,613 A | 5/1986 | Horii |
| 4,963,035 A | 10/1990 | McCarthy et al. |

(Continued)

FOREIGN PATENT DOCUMENTS

| | | |
|---|---|---|
| CN | 203018326 U | 6/2013 |
| EP | 2174552 A1 | 4/2010 |

(Continued)

OTHER PUBLICATIONS

United States Standards for Grades of Fresh and Frozen Shrimp, USDC/NOAA/Seafood Inspection Program.

(Continued)

*Primary Examiner* — Anh H Do
(74) *Attorney, Agent, or Firm* — James T. Cronvich

(57) ABSTRACT

Method and apparatus for grading food items, such as shrimps and chicken parts, with an automatically calibrated imaging system. Singulated food items are individually imaged. An estimated weight for each food item is computed from its image and an image-to-weight function. Calibration weighers weigh the food item individually or in batches before or after imaging. The actual weights are compared to the estimated weights to fine-tune the image-to-weight function and improve weight estimation.

25 Claims, 4 Drawing Sheets

(56) References Cited

U.S. PATENT DOCUMENTS

| | | | | |
|---|---|---|---|---|
| 4,979,418 | A | * | 12/1990 | Covert ................ B26D 3/11 408/111 |
| 5,201,259 | A | * | 4/1993 | Covert ................ B26D 3/11 83/422 |
| 5,244,100 | A | | 9/1993 | Regier et al. |
| 5,383,561 | A | | 1/1995 | Tokutu |
| 5,526,437 | A | | 6/1996 | West |
| 5,659,624 | A | | 8/1997 | Fazzari et al. |
| 6,808,448 | B1 | | 10/2004 | Kanaya et al. |
| 7,202,434 | B2 | | 4/2007 | Lofqvist et al. |
| 7,395,934 | B2 | | 7/2008 | Gudjonsson |
| 8,647,121 | B1 | * | 2/2014 | Witlin ............ G09B 19/0092 434/127 |
| 8,820,534 | B2 | | 9/2014 | Thorsson et al. |
| 8,985,341 | B2 | | 3/2015 | Lapeyre et al. |
| 9,145,268 | B2 | * | 9/2015 | Finnsson ............ B65G 21/14 |
| 9,314,206 | B2 | * | 4/2016 | Menczel ............ A61B 5/4866 |
| 2011/0317001 | A1 | | 12/2011 | Massen |
| 2014/0168411 | A1 | | 6/2014 | Ledet et al. |
| 2015/0020664 | A1 | | 1/2015 | Skyum et al. |

FOREIGN PATENT DOCUMENTS

| | | |
|---|---|---|
| JP | 04058373 A | 2/1992 |
| JP | H10-137695 A | 5/1998 |
| WO | 2005062994 A2 | 7/2005 |
| WO | 2010097684 A2 | 9/2010 |
| WO | 2010142413 A1 | 12/2010 |

OTHER PUBLICATIONS

Lizotte Nordic Shrimp Sorter brochure, Lizotte Machine Vision, Riviere-Verte, New Brunswick, Canada.

Inspector's Guidelines for Grading Fresh or Frozen Shrimp, Jan. 20, 1993.

Murat O. Balaban, Sencer Yeralan, Ymir Bergmann, "Determination of Count and Uniformity Ratio of Shrimp by Machine Vision," Journal of Aquatic Food Product Technology, vol. 3(3) 1994, Haworth Press, Inc.

International Search Report and Written Opinion of the International Searching Authority, PCT/US2016/016393, dated Apr. 20, 2016, Korean Intellectual Property Office, Daejeon, Republic of Korea.

* cited by examiner

VISION-BASED GRADING WITH AUTOMATIC WEIGHT CALIBRATION

BACKGROUND

The invention relates generally to grading or sizing and more particularly to vision-based grading of individual food items.

Food items that are individually processed without further subdivision, such as shrimps and chicken parts, often have to be sorted into grades by size or weight. Head-on, headless, and peeled shrimps, for example, are typically graded by weight using one of three methods:

A) by hand, where shrimps are placed into appropriate size-bins after their weights are visually approximated or individually weighed on a scale;

B) with checkweighers, such as weigh belts, where shrimps pass one at a time over a belt-covered scale before being conveyed through actuated gates into appropriate size-bins; or C) with mechanical devices that sort the shrimps based on their width, such as roller-gap graders where, by virtue of diverging gaps between adjacent rollers, larger shrimps progress farther down the inclined rollers before falling through the gaps into sequential size-bins.

All these approaches have significant drawbacks. Approach A is extremely slow if shrimps are individually weighed and inaccurate if size is visually approximated. Approach B permits faster weighing of individual shrimps, but checkweigher accuracy suffers when individual shrimps are weighed, and throughput is limited because only one shrimp can be accommodated at a time. Approach C permits much higher throughput, but is relatively inaccurate because correlation of shrimp weight to roller gap is affected by multiple variables, some controllable, such as roller speeds and water flow rates, and some uncontrollable, such as shrimp shape, texture, and firmness.

SUMMARY

A method embodying features of the invention for grading a food item comprises: (a) singulating a supply of individual food items; (b) imaging each of the food items to produce an image of each of the food items; (c) computing an estimated weight of each of the food items using an image-to-weight function; (d) weighing a sample of the food items to produce an actual weight of the weighed food items in the sample; (e) comparing the estimated weights to the actual weights; (f) adjusting the image-to-weight function based on the comparison of estimated weights to actual weights; and (g) grading the food item into a plurality of grades.

In another aspect of the invention, a grading system comprises an imaging system producing images of each of a supply of food items and a controller computing estimated weights of each of the food items from the images. The controller also computes an image-to-weight function and assigning each of the food items to one of a plurality of grades based on the estimated weight of the food item. A sorter sorts each of the food items into one of a plurality of grade channels based on the grade assigned to the food item. A calibration weigher in each of the grade channels produces actual weights of the food items in each of the grades. The controller adjusts the image-to-weight function based on a comparison of the estimated weights to the actual weights for each of the grades.

DETAILED DESCRIPTION

Figure 1:
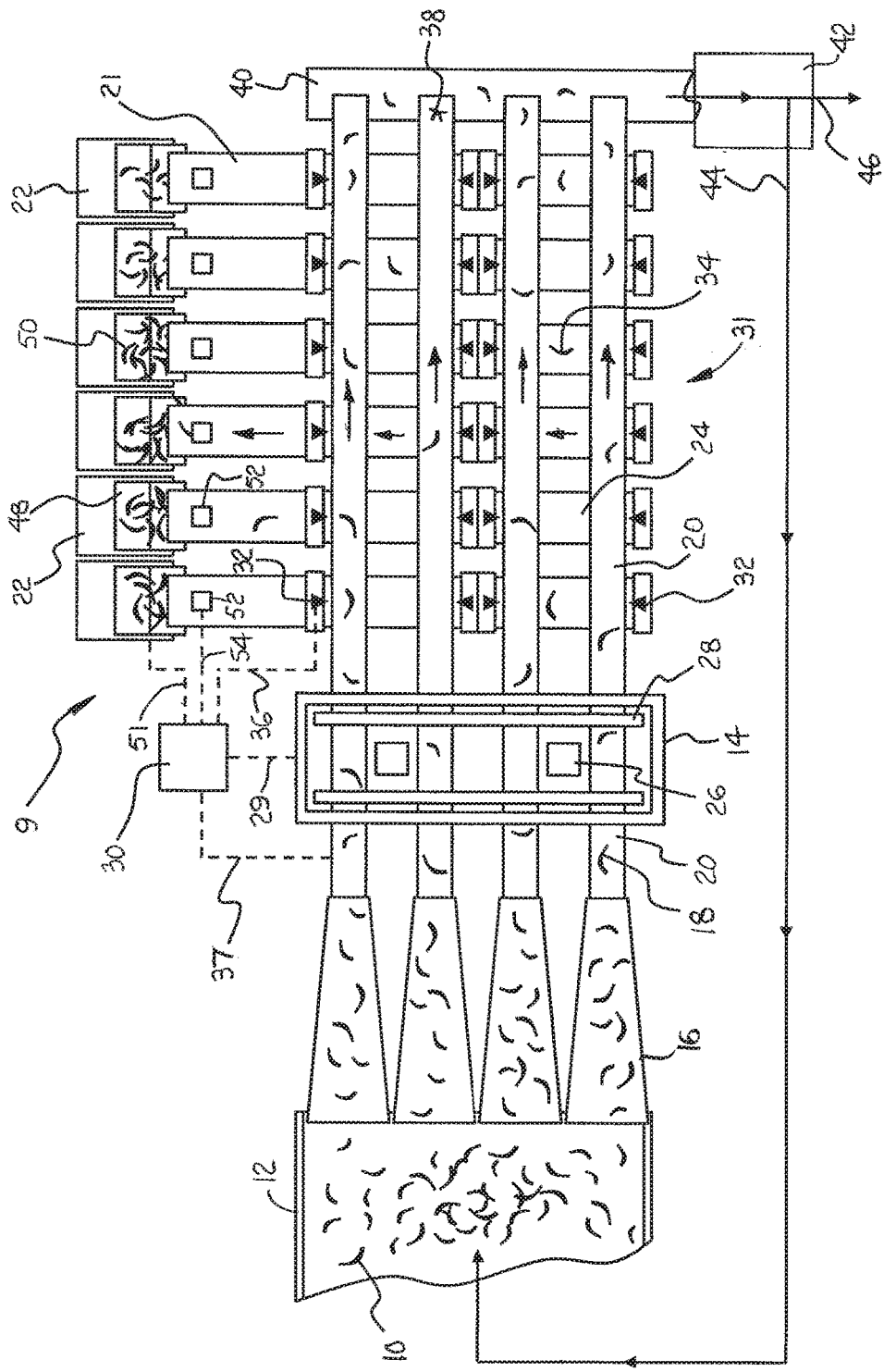
FIG. 1 is a top plan view of one version of a vision-based grading system embodying features of the invention.

One version of a grading system 9 for sorting individual food items, such as chicken parts and shrimps, into various grades is shown in FIG. 1. To simplify the description, grading of shrimp will be used as the example. A supply 10 of raw shrimps in a feed tank 12 is conveyed to an imaging system 14 over one or more—in this example, four—singulating conveyors 16, which form the shrimps 18 into a single file on individual transport lanes 20. The transport-lane conveyors transport the singulated shrimps 18 through the imaging system 14 to downstream grade channels 21 including grade bins 22 via output-lane conveyors 24.

The imaging system comprises one or more cameras 26 and one or more light sources 28 illuminating the shrimps 18 in the cameras' fields of vision. The cameras 26 produce images of the singulated shrimps 18. The digital images 29 are sent to a controller 30 that has image-processing capability. The controller 30 converts the two-dimensional (2D) projected area or the camera pixel count of each of the imaged shrimps into an estimated weight using an image-to-weight unction providing a conversion factor from image to weight. From the estimated weight the controller 30 assigns each of the shrimps to one of the grade bins 22. Each grade bin is the destination for shrimps whose estimated weights lie within a predetermined weight range, or grade. To improve the accuracy of the weight estimation, a three-dimensional (3D) imaging technique can be used to estimate each shrimp's volume, which is directly proportional to weight for shrimps of uniform mass density. One way to realize 3D imaging is by adding a side-view camera or laser curtain sensor to the imaging system 14 to detect a third dimension, i.e., the thickness, or height, of the shrimps 18 lying on the transport conveyors 20.

Alternatively, a pair of cameras offset by some angle can be used to stereoscopically image the shrimps. Or, as another example, a line-scanning laser system can be used as the camera to produce a 3D image of each shrimp. Additionally, the 3D topography of each shrimp can be recreated using one or more cameras to image and analyze the distortion of parallel or intersecting laser lines projected on the shrimp.

Regardless of whether 2D, 3D, or some other method for estimating the weight of each shrimp is used, vision-based weight grading offers other advantages. Attributes other than weight can be detected and measured. Whether a shrimp is whole or is missing a fraction of its meat, whether a shrimp has its telson attached or has excessive throat meat, and whether a shrimp has residual shell (which can be detected, for example, with a camera sensing UV, fluorescence) are examples of other attributes the imaging system can ascertain.

Sorting is effected downstream of the imaging system 14 in a sorter 31 by ejection actuators 32, such as solenoid-actuated air jets, which push the imaged shrimps 34 off the sides of the transport lanes 20 and onto the grade lanes 24. The controller 30 controls the ejection actuators 32 with ejection signals over ejection control lines 36 to divert each shrimp to its designated destination bin 22. With a priori knowledge of the speed of the transport conveyor 20 downstream of the imaging system 14, the controller 30 knows when to energize the actuators 32 to sort each shrimp 34 to the appropriate bin. The controller 30 can also adjust the speed of the transport conveyor 20 over control lines 37. Rejects 38, such as unrecognizable imaged items, shrimp bits, shrimps with residual shell or appendages, touching shrimps, and shrimps not meeting selected quality or size criteria, are conveyed off the end of the transport conveyors 20 and onto a return conveyor 40. Touching shrimps rejected for not being singulated, but otherwise acceptable, are culled from the other rejects at a culling station 42, and returned to the feed tank 12 by a recirculator 44, such as a conveyor, a flume, or a plant operator. Complete rejects 46 are removed from the grading system 9.

Because the estimated weight and the quality of every shrimp delivered to one of the output grade channels 21 are known, the controller 30 can track, trend, and display the total throughput through the grading system 9, the throughput of each grade or quality category, and the mean size and variance in each grade. The bounds and target mean of each grade range and an initial or manually adjusted image-to-weight function can be set by the user through the controller 30. Weight variability and quality metrics can be compared to user-defined statistical-process-control limits in real time to alert operators and take corrective control actions when the limits are exceeded. Weight and quality sorting criteria can be optimized to fill orders more profitably with graded shrimp based on customer-specified process-control limits and financial considerations, such as size-based shrimp costs and product prices. Multiple output lanes 24 can be configured by the controller 30 to handle a single grade to accommodate high throughput concentrations of certain size ranges.

The estimated weights of the shrimps are affected by variations in shrimp physiology due to natural causes or to handling, such as physical compression and moisture loss and gain. So, with a fixed image-to-weight function relating the image to an estimated weight, the error in the estimate can vary with changes in shrimp physiology. To minimize such estimation errors, the controller continually or periodically adjusts the image-to-weight function with each shrimp or batch of shrimps weighed. The mathematical domain of the image-to-weight function is made up of elements that are ranges of image sizes. Assigned to each element of the image-to-weight function's domain is a set of one or more conversion coefficients that are used in a conversion formula, such as a polynomial formula, to convert a shrimp's image size into an estimated weight. For a third-degree polynomial ($Ax^3+Bx^2+Cx+D$), the set would include four conversion coefficients A, B, C, D, where A, B, and C are multiplied by corresponding powers of the image size x and D is a constant term. For a purely linear relationship between image size and estimated weight, the set would include a single conversion value—corresponding to coefficient C in the polynomial in the preceding sentence with $A=B=D=0$. The number of sets of conversion coefficients equals the number of elements in the domain. For example, if the same conversion formula with the same set of conversion coefficients is used across all shrimp sizes, the domain includes only one element: the entire range of shrimp sizes. In that case the image-to-weight function is an adjustable constant. As another example, if all the shrimps in each grade use the same conversion formula with the same set of coefficients, but the conversion formulas or different conversion coefficients can differ from grade to grade, then the elements of the image-to-weight function's domain are the grades themselves. So if there are five grades (five domain elements), there would be five independently adjustable sets of conversion coefficients that define the image-to-weight function. It is also possible to have more or fewer domain elements than grades. In other words, the adjustable conversion formulas do not have to be aligned with the grades. In that case the entire range of shrimp image sizes is divided into contiguous image-size ranges unaligned with the grades, each size range constituting an element of the domain of the image-to-weight function. And to each of those size ranges (domain elements) a corresponding conversion formula or set of conversion coefficients is assigned. So, in that case, the image-to-weight function is composed of an adjustable set of conversion coefficients for each size range. It is also possible for the controller 30 to use interpolation techniques, such as linear interpolation, to improve the weight estimate. For example, assume the image-to-weight function has a domain of five grades (G1, G2, G3, G4, G5 in increasing order) and the conversion formula for each grade includes only a single conversion coefficient (C1, C2, C3, C4, C5). The estimated weight of a shrimp whose image has a size in the middle of grade G3 would be computed using the coefficient C3. But the weight of a shrimp whose image has a size in the lower half of grade G3 can be estimated by using a conversion coefficient interpolated between the values of coefficients C2 and C3. In this way interpolation can be used to enhance the estimation provided by the adjustable image-to-weight function. The conversion formulas can produce absolute weight estimates or offsets to nominal estimated weight values. Instead of being represented by a conversion formula, the image-to-weight function could be realized in a look-up table of image-to-weight values for consecutive image size ranges or pixel counts. And the image-to-weight values can be absolute values or offsets from nominal values.

As shown in FIG. 1, each grade channel 21 has an associated calibration weigher 48, which may be a weigh hopper or a weigh belt, for example. Shrimps 50 sorted to each grade bin 22 are weighed individual by the calibration weigher 48 or as a batch of shrimps accumulated in the bin. The calibration weigher 48 measures the actual weight of each shrimp or of a batch of shrimps and sends those weight values to the controller 30 over data lines 51. The controller compares the actual weight of each shrimp or of a batch of shrimps to the estimated weight of that shrimp or of the shrimps making up that batch. From that data the controller 30 computes an updated image-to-weight function that may be specific to that grade to be used in estimating the weights of imaged shrimps. When each batch in the grade bin 22 is complete, the controller 30 empties the bin to release the batch and start accepting a new batch. To confirm the arrival of shrimps at a given grade bin 22, a suitable cost-effective means, such as a low-resolution camera or laser curtain sensor 52 upstream of each bin, can signal the controller 30 over signal lines 54 that a shrimp has arrived. In this way shrimps that do not arrive at their designated destination bins are not used in the automatic adjustment of the image-to-weight function. And those missing shrimps are conveyed off the end of the transport conveyor with the other rejects 38.

Figure 2:
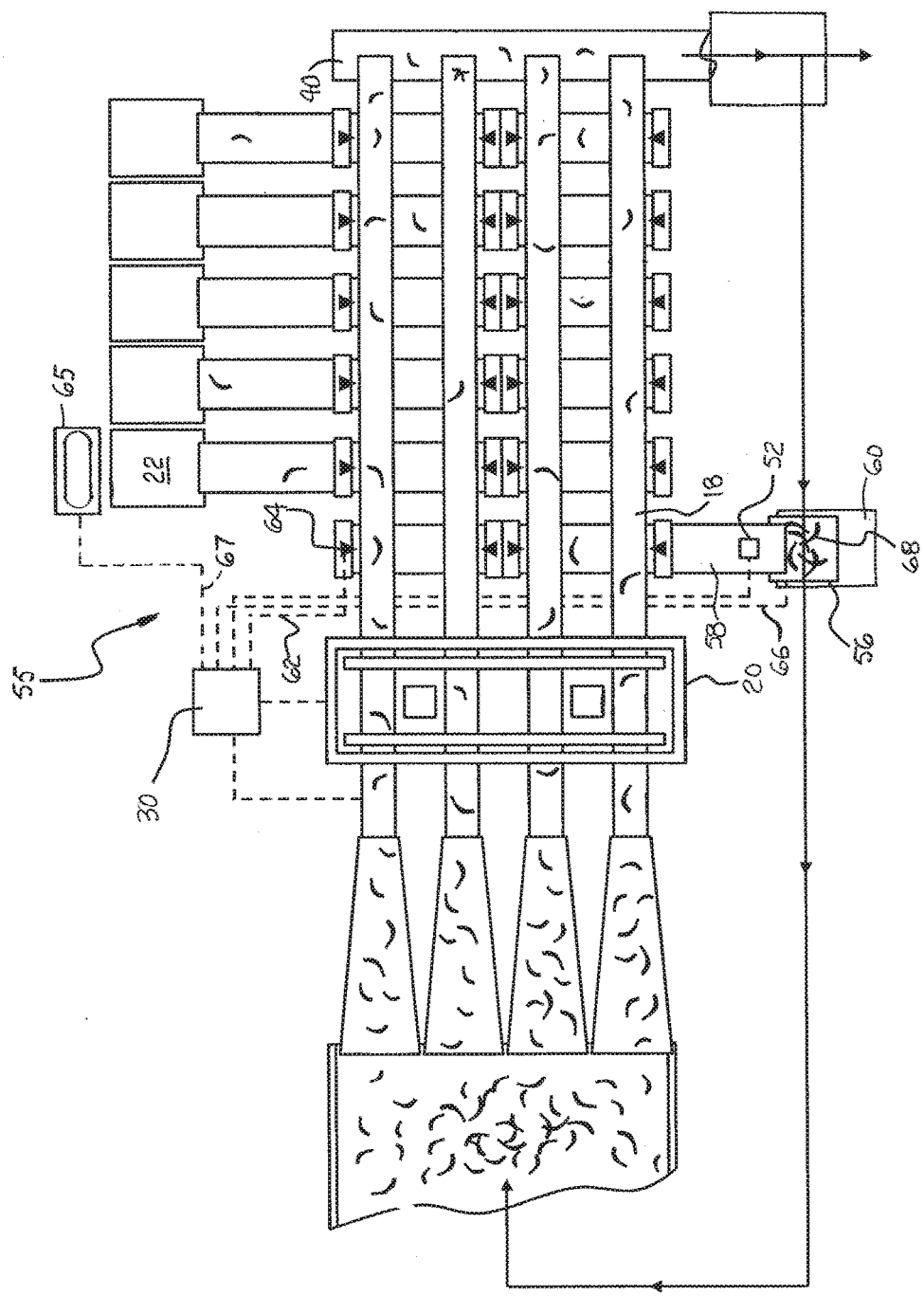
FIG. 2 is a top plan view of another version of a vision-based grading system embodying features of the invention, including a calibration channel.

The grading system 55 in FIG. 2 is similar to that of FIG. 1, except that it uses only a single calibration weigher 56 downstream of the imaging system 20. The single calibration weigher 56 is associated with a calibration channel 58 having a calibration bin 60. On a configurable scheduled or event-driven basis, the controller 30 actuates calibration-channel actuators 64 over a calibration line 62 to divert shrimps that conform to a configurable lot criterion, such as a selected grade or an element of the domain of the image-to-weight function, from the transport lanes 18 to the calibration channel 58. After the calibration weigher 56 measures the actual weight of each shrimp or of a batch of shrimps, the weight value is sent to the controller 30 over a data line 66. The controller 30 then compares the actual weight value to the estimated weight for each shrimp or batch of shrimps to compute an updated image-to-weight function that may be universal (applicable to all shrimps) or specific to shrimps conforming to the lot criterion. When the calibration batch 68 is completed, the bin 60 is emptied and ready for a new calibration batch. The controller 30 can divert conforming shrimps to the calibration channel 58 according to a round-robin schedule or can divert them according to a custom order by scheduling those lots that include more shrimps to be calibrated more frequently. With this approach only a small fraction of the total throughput of shrimps has to be diverted to the single calibration channel 58 to generate an ample number of image-estimated and actual-weight data pairs to enable frequent, accurate updating of the image-to-weight function. And because only one calibration weigher 56 is used in the version depicted in FIG. 2, it can be of higher quality than lower-quality calibration weighers 48 used in the multiple grade channels 21 illustrated in FIG. 1, to provide a lower-cost, higher-performance solution.

FIG. 2 also shows a video display 65 associated with one of the grade bins 22. A display system could include a single display to display information for all the grade bins, a dedicated display for each grade bin, or shared displays associated with neighboring grade bins. The display system informs an operator of various conditions of the shrimps in the bins as determined by the controller 30, which sends display data to the display 65 over a signal line 67. When used with a calibration weigher 56 as in FIG. 2 or with a calibration weigher 48 in the system 9 of FIG. 1, the video display could receive weight data directly from the calibration weigher. Examples of bin-specific or global displayed information are: (1) alarm conditions; (2) number of shrimps; (3) shrimp count per pound; and (4) uniformity ratio (the ratio of the total weight of the N largest shrimps in a batch to the total weight of the N smallest shrimps, where N is an integer representing typically up to 10% of the total number of shrimps in the batch). Information on rejected images (e.g., images of unusable material, such as legs, loose shell, antennas, tail fin, seaweed and other extraneous material; images of dehydrated, diseased, or abnormal shrimps; images of shrimps with black spot; images of shrimp meats with attached throats; images of improperly cleaned shrimps; images of shrimp pieces or broken or damaged shrimps; images of improperly peeled shrimps with residual shell or heads) could also be displayed on a display associated with the return conveyor 40.

Figure 3:
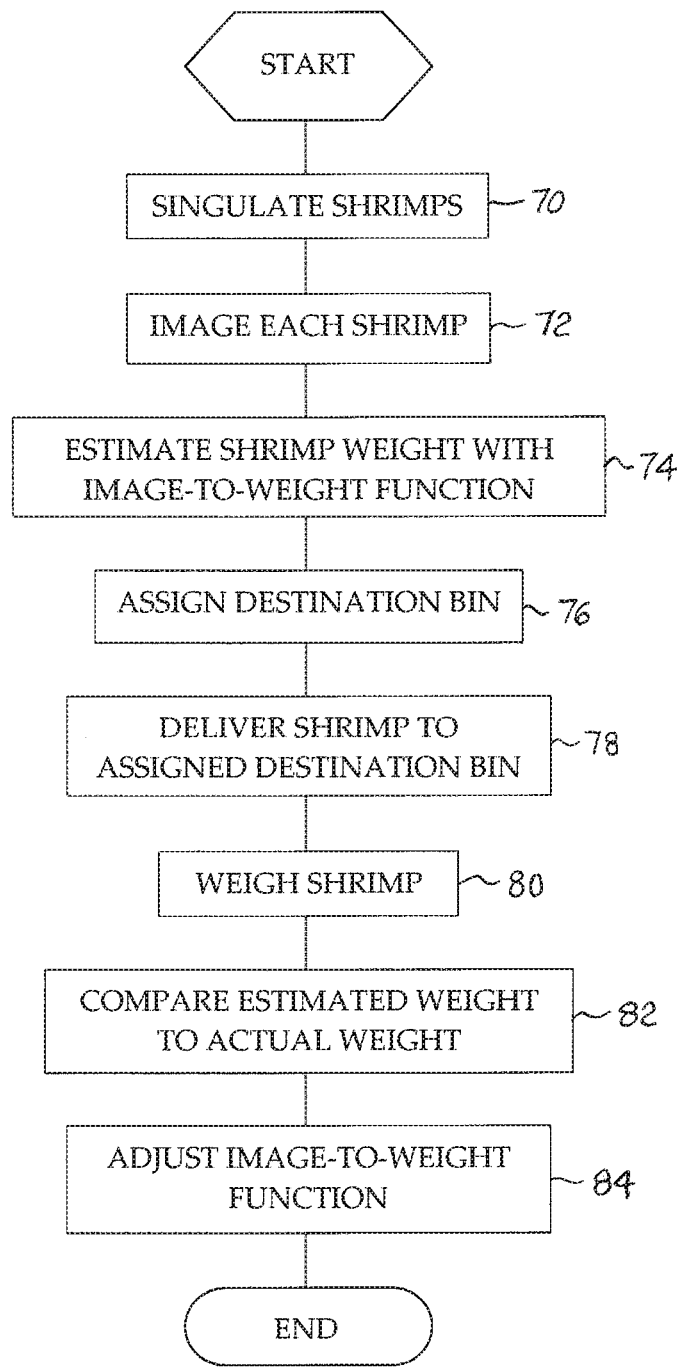
FIG. 3 is a flowchart of the operation of the grading system of FIG. 2 or FIG. 1.
Figure 4:
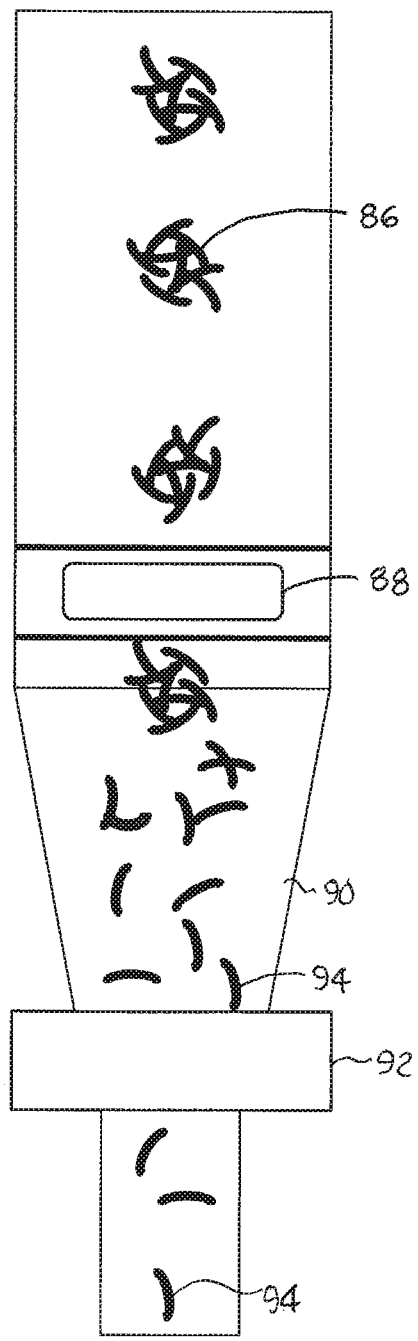
FIG. 4 is a block diagram of yet another version of a vision-based grading system embodying features of the invention and performing weighing before imaging.

The basic process is shown in the flowchart of FIG. 3. First, the shrimps are singulated 70 so that they can be individually imaged 72. From the image of each shrimp, its weight is estimated 74 with the image-to-weight function. A destination bin is assigned 76 to each imaged shrimp based on its estimated weight. Then the shrimp is conveyed 78 to its assigned destination bin. Each shrimp or a known number of shrimps in the destination bin are weighed 80. The actual weight measured is compared 82 to the estimated weight shrimp by shrimp or batch by batch. The image-to-weight function is adjusted 84 depending on the comparison. For example, if the actual weight exceeds the estimated weight, the image-to-weight function is adjusted to increase the estimated weight provided by the conversion formula for the corresponding domain element. One way the adjustment can be made is by recomputing the set of conversion coefficients with the additional actual weight information using a linear regression curve fit. If the image-to-weight function is stored in a look-up table of image-to-weight values for consecutive ranges of image pixel counts, individual image-to-weight values can be recomputed based on the additional weight information. If the estimated weight equals the actual weight, no adjustment to the image-to-weight function is made. An alternative version of a grading system is shown in FIG. 4. In this arrangement the shrimps are weighed before imaging. The shrimps are conveyed in separate batches 86 to a calibration weigher 88 that determines an actual weight of each batch. Then the shrimps in the batch are singulated in a singulator 90 and conveyed to an imaging system 92, which produces an image of each of the individual singulated shrimps 94. A controller, like that shown in FIGS. 1 and 2, uses the image and an image-to-weight function to estimate the weight of each singulated and imaged shrimp 94. The controller assigns each shrimp to its designated downstream grade channel (not shown in FIG. 4) and counts the number of shrimps in each batch. After comparing the accumulated estimated weights of the individual shrimps 94 in each batch 86 to the actual weight of the batch, the controller adjusts the image-to-weight function to improve subsequent weight estimations.

What is claimed is:

1. A method for grading a food item comprising:
singulating a supply of individual food items with a singulating conveyor;
imaging each of the food items with an imaging system to produce an image of each of the food items;
computing in a controller an estimated weight of each of the food items using an image-to-weight function;
weighing a sample of the food items with a calibration weigher to produce an actual weight of the weighed food items in the sample;
comparing the estimated weights to the actual weights in the controller;
adjusting the image-to-weight function in the controller based on the comparison of estimated weights to actual weights;
grading the food item into a plurality of weight grades with a sorter.

2. The method of claim 1 comprising grading the food items into the plurality of weight grades by sorting each of the food items by estimated weight to calibration weighers, one for each of the grades.

3. The method of claim 2 comprising weighing the food items in the calibration weighers individually or in batches.

4. The method of claim 1 wherein the sample of the food items is a subset of all the food items.

5. The method of claim 1 comprising weighing the sample of the food items before singulating the food items.

6. The method of claim 1 wherein the estimated weights are compared to the actual weights for each of the food items individually or in batches.

7. The method of claim 1 further comprising counting the individual food items.

8. The method of claim 1 further comprising diverting food items of a selected estimated weight range during a calibration period to a calibration weigher.

9. The method of claim 1 further comprising detecting unsingulated food items and recirculating the unsingulated food items back into the supply of food items to be singulated.

10. The method of claim 1 wherein the image of the food items is a two- or three-dimensional image.

11. The method of claim 1 wherein the image of the food items is a composite three-dimensional image combining a two-dimensional image with a third measured dimension of the food items.

12. The method of claim 1 wherein the image-to-weight function is adjustable for each of the plurality of weight grades.

13. The method of claim 1 wherein the image-to-weight function is adjustable for ranges of estimated food-item weights not aligned with the weight grades.

14. The method of claim 1 further comprising displaying information associated with each of the weight grades.

15. The method of claim 1 further comprising rejecting items not recognizable as acceptable food items.

16. A grading system comprising:
an imaging system producing an image of each of a supply of food items;
a controller computing estimated weights of each of the food items from the image of the food item and an image-to-weight function and assigning each of the food items to one of a plurality of weight grades based on the estimated weight of the food item;
a sorter sorting each of the food items into one of a plurality of grade channels based on the weight grade assigned to the food item;
a calibration weigher in each of the grade channels producing actual weights of the food items in each of the weight grades;
wherein the controller adjusts the image-to-weight function based on a comparison of the estimated weights to the actual weights for each of the weight grades.

17. A grading system as in claim 16 wherein the calibration weigher in each grade channel produces an actual weight for each of the food items sorted to that grade channel.

18. A grading system as in claim 16 wherein the calibration weigher in each grade channel produces an actual weight of a batch of the food items sorted to that grade channel.

19. A grading system as in claim 16 further comprising a singulator singulating the supply of food items for delivery to the imaging system.

20. A grading system as in claim 19 further comprising a recirculator recirculating unsingulated food items back to the singulator for singulating.

21. A grading system as in claim 16 wherein the controller counts the food items assigned to each of the weight grades.

22. A grading system as in claim 16 further comprising a display system displaying information associated with each of the grade channels.

23. A grading system comprising:
an imaging system producing an image of each of a supply of food items;
a controller computing estimated weights of each of the food items from the image of the food item and an image-to-weight function and assigning each of the food items to one of a plurality of weight grades based on the estimated weight of the food item;
a sorter sorting each of the food items into one of a plurality of grade channels based on the weight grade assigned to the food item;
a calibration channel including a calibration weigher to which the sorter sorts food items of a selected estimated weight range during a calibration period, wherein the calibration weigher produces an actual weight of a batch of food items of the selected estimated weight range;
wherein the controller adjusts the image-to-weight function by comparing the actual weight to the estimated weight of the food items sorted to the calibration channel.

24. A grading system as in claim 23 wherein the estimated weight range coincides with one of the weight grades.

25. A grading system comprising:
a calibration weigher determining an actual weight of a batch of food items;
a singulator singulating the batch of food items weighed by the calibration weigher;
an imaging system producing an image of each of the singulated food items;
a controller computing estimated weights of each of the food items from the image of the food item and an image-to-weight function and assigning each of the food items to one of a plurality of weight grades based on the estimated weight of the food item;
a sorter sorting each of the food items into one of a plurality of grade channels based on the weight grade assigned to the food item;
wherein the controller adjusts the image-to-weight function by comparing the actual weight to the estimated weight of the food items.

* * * * *